(12) United States Patent  
Kressner

(10) Patent No.: US 7,765,629 B2  
(45) Date of Patent: Aug. 3, 2010

(54) ELECTRIC TOOTHBRUSH AND CORRESPONDING TOOTHBRUSH HEAD

(75) Inventor: Gerhard Kressner, Altenstadt (DE)

(73) Assignee: Braun GmbH, Kronberg (DE)

( * ) Notice: Subject to any disclaimer, the term of this patent is extended or adjusted under 35 U.S.C. 154(b) by 1292 days.

(21) Appl. No.: 10/535,163

(22) PCT Filed: Nov. 3, 2003

(86) PCT No.: PCT/EP03/12213  
§ 371 (c)(1),  
(2), (4) Date: May 16, 2005

(87) PCT Pub. No.: WO2004/045448  
PCT Pub. Date: Jun. 3, 2004

(65) Prior Publication Data  
US 2006/0048314 A1  Mar. 9, 2006

(30) Foreign Application Priority Data  
Nov. 16, 2002  (DE) ................................ 102 53 532

(51) Int. Cl.  
*A61C 17/22* (2006.01)

(52) U.S. Cl. ................... 15/22.2; 15/22.1; 15/22.4

(58) Field of Classification Search ............ 15/22.1, 15/22.2, 22.4, 28  
See application file for complete search history.

(56) References Cited

U.S. PATENT DOCUMENTS

| | | | | |
|---|---|---|---|---|
| 4,766,633 A | * | 8/1988 | Clark | 15/167.1 |
| 5,504,958 A | * | 4/1996 | Herzog | 15/22.1 |
| 5,504,959 A | | 4/1996 | Yukawa et al. | |
| 5,524,312 A | | 6/1996 | Tan et al. | |
| 5,652,990 A | * | 8/1997 | Driesen et al. | 15/28 |
| 6,434,773 B1 | * | 8/2002 | Kuo | 15/22.1 |
| 6,725,490 B2 | * | 4/2004 | Blaustein et al. | 15/22.2 |

FOREIGN PATENT DOCUMENTS

EP   1 093 770   4/2001

* cited by examiner

*Primary Examiner*—Laura C Guidotti  
(74) *Attorney, Agent, or Firm*—John P. Colbert; Valdimir Vitenberg

(57) ABSTRACT

A toothbrush head of an electric toothbrush, which comprises a handpiece equipped with a drive, a brush head carrier that is connectible to the handpiece, and several bristle supports that carry a respective bristle set, are movably mounted on the brush head carrier and drivable in an oscillatory manner by the drive, each of the bristle supports being adapted to be coupled to a translator element of the drive by means of a respective drive coupling. According to the invention the bristle supports each have drive coupling means enabling them to be coupled to eccentric drivers of the drive translator element which is adapted to be driven for rotation about a longitudinal axis. Owing to the arrangement of two separately mounted bristle supports which are driven by a common drive translator element about various axes of motion, it is possible to achieve an improved cleaning effect by simple means. The relative movement of the bristle sets that are mounted on the bristle supports assists the cleaning motion so that the cleaning effect is not obtained solely by the operator's movement.

22 Claims, 7 Drawing Sheets

(B-B)

(D-D)

ELECTRIC TOOTHBRUSH AND CORRESPONDING TOOTHBRUSH HEAD

TECHNICAL FIELD

This invention relates to a toothbrush head of an electric toothbrush.

BACKGROUND

U.S. Pat. No. 5,524,312 discloses an electric toothbrush on whose brush head provision is made for two separate brush holders which are driven by a common transmission rod. The one brush holder performs an oscillating rotary motion about an axis perpendicular to the brush neck. The other brush holder is pivoted back and forth about an axis parallel to the brush neck. This arrangement of brush holders brings about an active relative movement between the tufts of bristles but is disadvantageous inasmuch as it is restricted to a special drive mechanism. The additional brush holder arranged further to the rear of the handle requires a cylindrical bottom side with a special, curved guide groove in which an engaging projection of the transmission rod, which oscillates in longitudinal direction, engages. Furthermore, the configuration of the tufts of bristles arranged on the two brush holders is hardly suitable for the efficient cleaning of interproximal spaces.

SUMMARY

The toothbrush as disclosed is an improved toothbrush head and a corresponding improved toothbrush which avoid the disadvantages of the prior art and develop it further in advantageous manner. An improved cleaning of the teeth is to be achieved by using a simple, effective drive of the two bristle supports.

According to the invention the bristle supports each have drive coupling means enabling the bristle supports to be coupled to one or more eccentric drivers of the drive translator element which is adapted to be driven for rotation about a longitudinal axis. Owing to the arrangement of two separately mounted bristle supports which are driven by a common drive translator element about various axes of motion, it is possible to achieve an improved cleaning effect by simple means. The relative movement of the bristle sets that are mounted on the bristle supports assists the cleaning motion so that the cleaning effect is not obtained solely by the operator's movement.

The eccentric drivers of the translator element for driving the bristle supports may be variously constructed. According to one embodiment the bristle supports are adapted to be coupled to a common driver pin, which describes a cylindrical or conical orbit relative to the rotation axis of the translator element and may be assigned to the handpiece of the toothbrush. Alternatively each bristle support could be provided with its own driver pin on the translator element, the one being able to describe a conical orbit and the other a cylindrical orbit. However, provision is made for only one common driver pin for both bristle supports, with said pin describing a cylindrical drive motion.

The driver pin is driven to oscillate so that only a partial orbit is described, which may be in the shape of a cylinder segment or a cone segment. It is thus easily possible to obtain a corresponding oscillating motion of the two bristle supports. However, the driver pin could also describe a continuous, complete orbit in the manner of a crank, which like a crank drive brings about an oscillating motion of the bristle supports. It is preferred, however, for the translator element may oscillate with its eccentric drivers within an angle segment of ±90° or less.

In a further aspect the translator element is permanently assigned to the toothbrush head and mounted on the brush head carrier for rotation about its longitudinal axis in the interior of the brush head carrier. To be able to remove the toothbrush head from the handpiece of the toothbrush, the translator element may have on its end close to the handpiece a coupling section that forms a releasable rotary coupling for the non-rotatable coupling to a drive element at the handpiece end. The brush head carrier, which forms a brush tube, has on its end remote from the bristle supports releasable fastening means for its attachment to the handpiece of the toothbrush. When the brush head carrier is seated on the handpiece of the toothbrush, the drive translator element provided in the brush head carrier and the drive element at the handpiece end are coupled to each other at the same time.

In a further aspect the bristle supports are all mounted on the brush head carrier for movement about or along an axis of motion transverse to the longitudinal direction of the toothbrush, whereby each bristle support has its own axis of motion which are arranged in spaced relationship to each other. Hence it is a characteristic of the toothbrush head that two bristle supports mounted for movement about separate transverse axes are driven by a common drive translator element. Irrespective of the concrete construction of the drive translator element, such a toothbrush head configuration affords particular advantages for the effective cleaning of the teeth.

In particular it is possible to provide for two bristle supports. One main bristle support, which may be arranged on the end of the brush head carrier remote from the handpiece of the toothbrush, may be mounted for rotation about an axis of rotation essentially perpendicular to the longitudinal direction of the toothbrush and essentially parallel to the main direction of the bristles provided on the main bristle support, and is adapted to be driven in oscillatory manner by the eccentric driver of the drive axis. The main bristle support may be essentially constructed in plate shape and have a circular contour. Alternatively, it is drivable in oscillating rotational manner about its axis of symmetry. As the case may be, a poking motion along the axis of rotation of the main bristle support can be superimposed on the rotational oscillating drive motion in order to obtain a more thorough cleaning of the interproximal spaces. For this purpose the main bristle support may be displaceably mounted on the brush head carrier in the direction of its axis of rotation.

Provided adjacent to the main bristle support may be an auxiliary bristle support that is arranged in direct proximity behind the main bristle support, meaning closer to the handpiece of the toothbrush. The auxiliary bristle support may have various axes of motion. According to a one embodiment the auxiliary bristle support is pivotally mounted about a pivot axis arranged essentially perpendicular to the longitudinal direction of the toothbrush, and may be driven in oscillatory manner by the drive translator element, which also drives the main bristle support.

According to an embodiment the pivot axis is arranged in off-center position relative to the auxiliary bristle support or the bristle set arranged on it in order to obtain a larger movement on a section of the bristle support opposite the pivot axis. The pivot axis of the auxiliary bristle support may be arranged approximately parallel to the main direction of the bristles and hence parallel to the axis of rotation of the main bristle support. If the axis is arranged in longitudinal direction of the toothbrush on an edge section of the auxiliary bristle support, the opposite edge section of the auxiliary bristle support performs a reciprocating motion in transverse direction. Basically it would also be possible to arrange the pivot axis in center position relative to the auxiliary bristle support such that the latter rotates about its own center like the main bristle support. Another embodiment is the arrangement of the pivot axis in particular on the end of the auxiliary bristle support close to the main bristle support so that the bristles anchored to the auxiliary bristle support closer to the handpiece may move transversely in a reciprocating motion and wipe the interproximal spaces clear.

In an alternative further aspect the pivot axis of the bristle support may lie essentially in the plane defined by the auxiliary bristle support and extend perpendicular to the longitudinal direction of the toothbrush. Accordingly, the auxiliary bristle support performs an up and down rocking motion such that its tufts of bristles move up and down in a poking action. This rocking axis of the auxiliary bristle support may extend, relative to the longitudinal dimension of the auxiliary bristle support, approximately centrally in longitudinal direction of the toothbrush, such that the rear end and the front end of the auxiliary bristle support rock up and down in counter sequence. In an alternative embodiment the rocking axis of the auxiliary bristle support may also be displaced towards one end of the auxiliary bristle support. In particular the auxiliary bristle support may be mounted on the brush head carrier for rocking motion about its end close to the handpiece, with the result that the tufts of bristles anchored in the auxiliary bristle support adjacent to the main bristle support perform an up and down poking motion. The interproximal spaces adjacent to the tooth flanks worked by the bristle set of the main bristle support can thus be cleaned particularly effectively.

However, it is not compulsory for the auxiliary bristle support to be pivotally mounted. According to another embodiment it is possible to provide for the auxiliary bristle support to be mounted on the brush head carrier for translational displacement along a motion axis. The corresponding sliding guide of the auxiliary bristle support may have a degree of freedom in a direction transverse to the longitudinal direction of the toothbrush.

To enable the bristles arranged on the auxiliary bristle support to perform a poking motion in longitudinal direction of the bristles, the translational motion axis of the auxiliary bristle support may lie essentially perpendicular to the plane defined by the auxiliary bristle support, i.e., essentially parallel to the main bristle direction defined by the bristles. Alternatively, the axis of motion transverse to the longitudinal direction of the toothbrush may lie in the plane defined by the auxiliary bristle support, thus enabling the auxiliary bristle support to be moved back and forth transversely. This enables the bristles arranged on the auxiliary bristle support to be moved in the direction of the interproximal spaces, wiping them clear.

The drive couplings between the two bristle supports and the eccentric driver of the drive shaft may be constructed as flexible couplings, each having a joint axis transverse to the longitudinal direction of the toothbrush. Insofar as the bristle supports do not make a translational reciprocating motion but a pivoting motion at their coupling points with the driver pin that maintains its spatial orientation, the corresponding angle offset may be compensated by the flexible coupling between the bristle supports and the eccentric driver.

In a further aspect the flexible couplings between the drive translator element and the bristle supports have at least one further degree of freedom in addition to their flexibility. On the one hand the drive coupling of one bristle support, particularly of the auxiliary bristle support, may be constructed such that only forces and movements transverse to the longitudinal direction of the toothbrush are transmitted. No forces are transmitted in the longitudinal direction of the toothbrush. This advantageously enables compensation of the relative movement developing between the driver pin and the bristle support in the longitudinal direction of the toothbrush.

To transmit the cylindrical or conical drive motion of the driver pin only partly to the bristle supports, the flexible coupling between the driver pin and the bristle supports may also have a degree of freedom transverse to the longitudinal direction of the toothbrush. In particular the connection between the eccentric driver and the auxiliary bristle support and/or the main bristle support may be constructed to be free-moving in a direction transverse to the plane of motion in which the respective bristle support is to move. The driver pin moving on a cylindrical or conical path thus transmits only one component of its oscillatory orbital motion to the respective bristle support. If, for example, the auxiliary bristle support is to be pivoted about an axis perpendicular to the auxiliary bristle support, i.e., parallel to the bristles, then the eccentric driver may sit in a longitudinal slot parallel to the direction of the bristles in the auxiliary bristle support. The motion component transverse to the longitudinal direction of the bristles is transmitted to the bristle support whereas the motion component of the driver pin parallel to the longitudinal direction of the bristles is not transmitted. If, by contrast, the auxiliary bristle support is to be rocked up and down, then the driver pin may sit in a transverse slot parallel to the bristle support plane, as the result of which the corresponding section is moved up and down while however the transversely reciprocating motion is not transmitted.

However, the driver pin does not have to sit in a slot-shaped recess in the auxiliary bristle support. Alternatively, the auxiliary bristle support may have as drive coupling a sliding surface that extends transverse to the longitudinal direction of the toothbrush and on which the driver pin slides. In this case it is possible to provide a biasing device in the form of a spring, for example, which urges the auxiliary bristle support with its sliding surface into contact with the driver and holds it engaged therewith. However, under certain circumstances it is also possible to dispense with such a biasing device because the auxiliary bristle support is automatically urged into engagement with the driver by the reaction forces from cleaning the teeth, as is the case, for example, when the auxiliary bristle support is to be rocked up and down with a poking motion.

In this arrangement the amplitude of the stroke of the bristle support can be influenced by the shape of the sliding surface. A further aspect the engaging sliding surface of the auxiliary bristle support may be of an essentially plane configuration. The drive motion of the eccentric driver has two components acting perpendicularly to each other, with the result that the driver slides back and forth on the sliding surface while simultaneously acting in perpendicular direction upon the sliding surface and moving the bristle support accordingly. The stroke of the bristle support then corresponds to the motion component of the driver perpendicular to the sliding surface.

If, on the other hand, a bigger—or smaller—stroking motion of the bristle support is desired, then the sliding surface may have a cam-shaped curvature transverse to the longitudinal axis of the translator element. When the eccentric driver moves back and forth over the sliding surface, the cam-shaped curvature generates the desired additional motion perpendicular to the back and forth motion.

A further aspect, the drive coupling means of one of the bristle supports, particularly the main bristle support, transmit forces both in the longitudinal direction of the toothbrush and in a direction transverse to the longitudinal direction of the toothbrush, with the corresponding driver being mounted on the translator element for displacement in the longitudinal direction of the toothbrush and being elastically biased. In particular the driver pin and the main bristle support may be biased against each other and/or against the tubular brush head carrier. The advantage thereby achieved is that no free movements and no rattling noises can arise in spite of the flexibility and in spite of the degrees of freedom of the drive coupling. The drive runs quietly.

Another aspect the translator element, which may be constructed as a plastic injection molding, has an eccentric bearing bore in which the driver pin, which may be constructed as a metal pin, is mounted for longitudinal displacement and for rotation about its longitudinal axis. To bias the driver pin against the bristle support a spring may sit on the driver pin and take support upon the translator element.

To make better use of the driven motion of the two bristle supports or the bristle sets arranged on them and to make the cleaning of the teeth even more effective, several clusters of bristle tufts tilted in varying orientations may be fastened to the main bristle support and/or the auxiliary bristle support. In this arrangement the clusters of bristle tufts tilted in varying orientations may be of varying cross sections and/or be constructed with various properties such as a different level of rigidity, length of bristle, height of bristle and the like. Alternatively, the bristle tufts arranged on the main bristle support are tilted in directions different from the bristle tufts on the auxiliary bristle support. According to an embodiment, bristle tufts tilted at varying angles may be provided on each bristle support.

It has proven expedient to provide not only bristle tufts with a circular cross section but also bristle tufts with a non-circular cross section, in particular an elongated, oval or rectangular cross section.

To be better able to penetrate the interproximal spaces, bristle tufts whose free working ends lie at various heights above the bristle supports may be provided on the main bristle support and/or on the auxiliary bristle support.

Additional advantages, application possibilities and advantageous features of this invention will become apparent from the subsequent description of embodiments, which are depicted in the Figures of the accompanying drawings. In this context, all features described or depicted, whether individually or in any combination, constitute the subject-matter of this invention, irrespective of their summary in the claims or the cross references of the latter and irrespective of their wording and representation in the description and the drawings, respectively.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
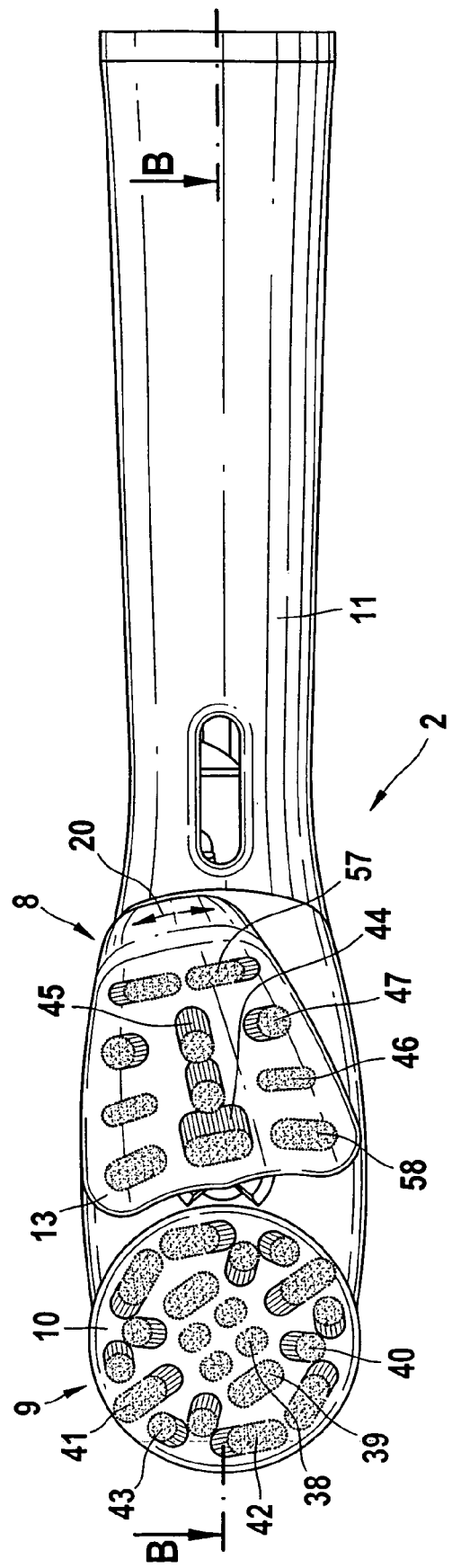
FIG. 1 is a top plan view of the replaceable toothbrush head of an electric toothbrush according to a first embodiment, showing two movably mounted bristle supports, each mounted and adapted to be driven for pivotal motion about a pivot axis parallel to the main direction of the bristles.

The toothbrush head 2 shown in FIG. 1 comprises a brush tube 11 which forms a brush head carrier and is attachable with an end thereof to a handpiece, not shown in detail, of an electric toothbrush. The handpiece includes in known manner a toothbrush housing in which a battery holding compartment and a drive motor are axially arranged one behind the other.

The brush head 2 has two bristle sets, namely a main bristle set 9 lying directly at the head end and a rear auxiliary bristle set 8 that lies in direct proximity of the main bristle set 9 at its end close to the handpiece.

Figure 2:
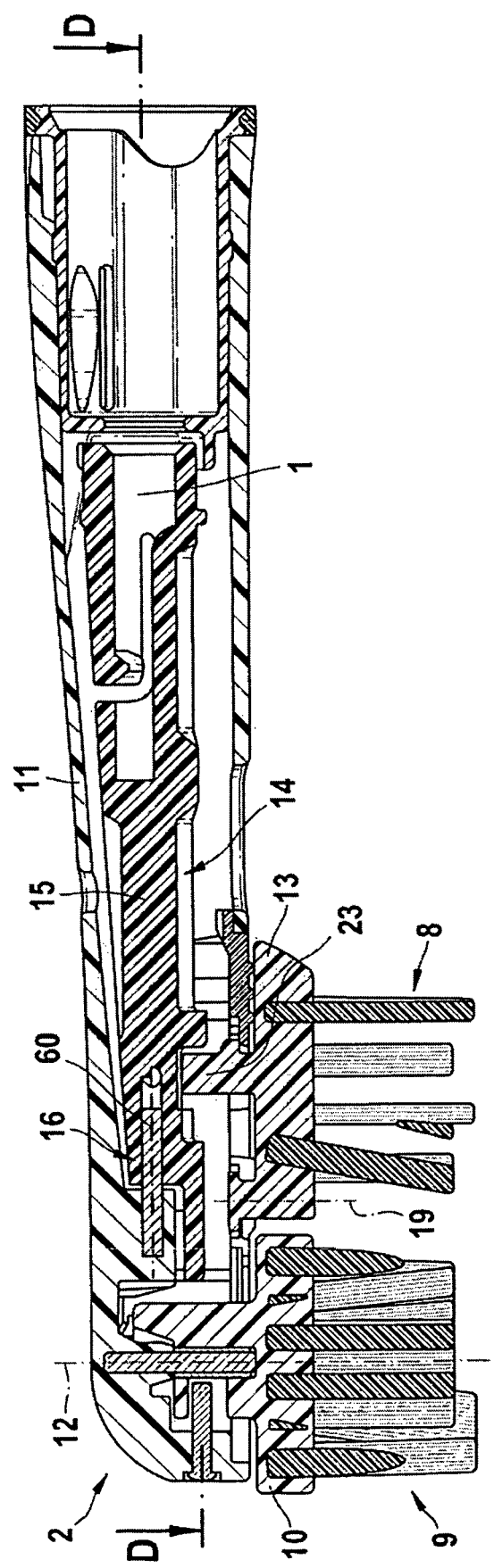
FIG. 2 is a vertical longitudinal section taken along the line B-B of the toothbrush head of FIG. 1, showing the mounting of the drive translator element which drives the two bristle supports.

As FIG. 2 shows, the bristle set 9 lying at the head end is carried by a main bristle support 10 which in the direction of the bristle set is constructed roughly like a circular plate and is fastened to a head section of the brush head carrier 11. As FIGS. 1 and 2 show, the bristle support 10 is rotatably seated on a spindle 12 which is anchored in the brush head carrier 11 and extends perpendicular to the longitudinal axis of the toothbrush roughly parallel to the main bristle direction of the bristle set 9. The spindle 12 defines the axis of symmetry of the plate-shaped bristle support 10.

The bristle support 10 is driven in an oscillatory rotary movement about the axis of rotation 12 by the motor, employing a translator element 14 in the form of a drive shaft 15. The drive shaft 15 is a plastic injection molding and is carried in the brush tube 11 in a bearing 16 which may be formed by a metal pin having its one end seated in a bearing section of the brush head carrier 11 and its other end in the drive shaft 15 in the longitudinal direction of the toothbrush. The bearing 16 permits the drive shaft 15 to rotate about its longitudinal axis 60 extending parallel to the longitudinal axis of the toothbrush. The drive shaft 15 is powered by a rotationally oscillating drive element which is connected by gearing to the motor shaft which extends in the longitudinal direction of the toothbrush. The drive shaft 15 performs an oscillating rotary motion. At its end close to the handpiece the drive shaft has a coupling section 1 enabling it to be plugged on a drive element on the handpiece in a manner preventing relative rotation.

Figure 4:
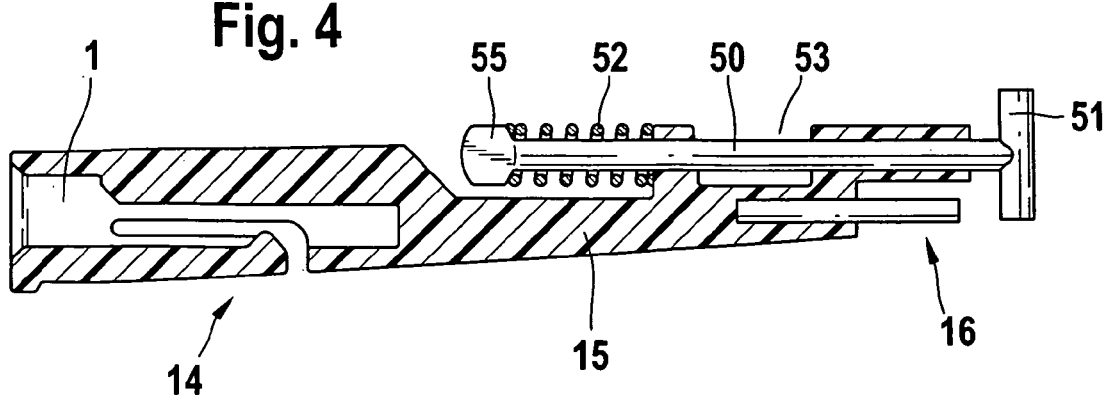
FIG. 4 is a longitudinal section of the drive translator element mounting the eccentric driver pin from the preceding Figures.

As FIG. 4 shows, provision is made in the drive shaft 15 for a passage hole extending approximately parallel to and at a distance from its longitudinal axis, in which a driver pin 50 is accommodated for rotation and longitudinal displacement. On its front end the driver pin 50 has a stud-shaped pickup 51 which extends at roughly right angles to the driver pin 50 and may be rigidly connected thereto, for example by welding.

The driver 50 performs a rotational orbital movement on a path shaped like a cylinder segment about the longitudinal and rotation axis of the drive shaft 15, with the plane of symmetry of the oscillating pivoting motion from which the driver is displaced to the right and left forming the plane of longitudinal symmetry of the toothbrush head 2.

The end of the driver pin 5, or the pickup 51 fastened thereto, close to the bristle support 10 sits in a blind-hole-shaped recess 18 in the bristle support 10, said recess being constructed in a segment of the bristle support 10 close to the handpiece and extending essentially parallel to the axis of rotation 12 (cf. FIG. 3), forming a drive coupler for bristle support 10. On account of the blind-hole-shaped recess only the component of the drive motion of the driver 50 transverse to the axis of rotation 12 is transmitted onto the bristle support 10. The up and down motion, i.e., the component of the orbital drive motion parallel to the axis of rotation 12, is not transmitted because the pickup 51 in the recess 18 is free-moving, i.e., longitudinally displaceable, parallel to the axis of rotation 12. Furthermore the mount of the pickup 51 in the recess 18 forms a rotary joint in order to compensate the oscillating angle offset between the bristle support 10 and the driver 50.

As FIG. 4 shows, the end of the driver pin 50 remote from the pickup 51 projects out of the passage hole in the drive shaft 15, protruding by some length beyond an edge of the drive shaft 15. A helical compression spring 52 is mounted on the driver pin 50 in the region of the projecting length. The free end of the driver pin 50 is compressed and flattened, forming a radial enlargement 55. The helical spring 52 thus rests against the enlargement and is held by it. Furthermore the helical compression spring 52 bears with its other end against the edge of the drive shaft 15. The helical compression spring 52 thus biases the driver pin 50 axially against the bristle support 10 in order to prevent rattling noises during use. Considering that the pickup 51 is seated in the blind-hole-shaped recess 18 in the bristle support 10, the pickup 51 performs an oscillating motion in a circular path about the axis of rotation 12 of the bristle support 10. The driver pin 50 is accordingly displaced in axially oscillating manner in the passage hole in the drive shaft 15, with the helical compression spring 52 being alternately compressed and extended in the process.

As FIGS. 1 and 2 show, the rear bristle set 8 near the handpiece is carried by a roughly plate-shaped auxiliary bristle support 13 which like the main bristle support 10 is movably mounted on the brush head carrier 11 independently of the drive translator element 15. As FIG. 2 shows, the auxiliary bristle support 13 has its forward edge portion at the end close to the main bristle support 10 pivotally mounted about a pivot axis 19 that extends essentially perpendicular to the longitudinal direction of the toothbrush and perpendicular to the plane defined by the auxiliary bristle support 13. Hence the auxiliary bristle support 13, in particular its portion at the end remote from the main bristle support 10, is able to pivot transversely back and forth as indicated by the arrow 20. It will be understood, of course, that it is not only possible for the bristle support 13 to be pivoted in the previously mentioned plane but that it is also possible for the bristle support 13 to be pivoted on the arc of a circle that is arranged congruently to the circular arc of the eccentric driver pin 50. As such, only one additional degree of freedom of motion relative to the pivot axis 19 needs to be provided for the bristle support 13.

Figure 3:
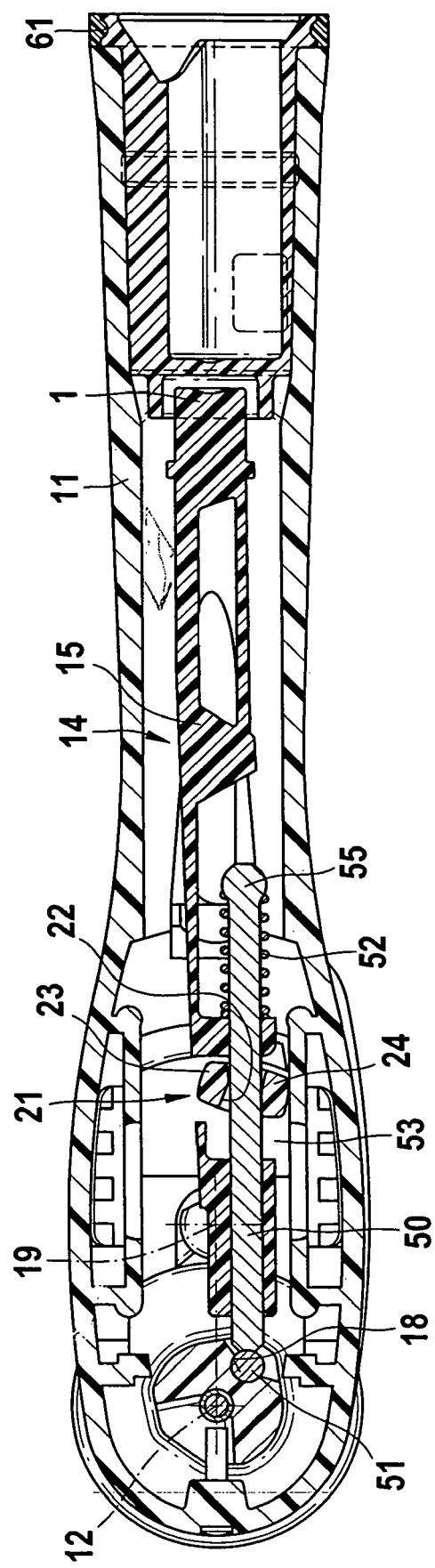
FIG. 3 is a horizontal longitudinal section taken along the line D-D of the toothbrush head of FIG. 2, showing the drive mechanism and in particular the coupling of the two bristle supports to an eccentric driver pin of the drive translator element.

To drive the auxiliary bristle set 8 in an oscillatory rotary movement about the pivot axis 19, the auxiliary bristle support 13 is coupled to the eccentric driver 50 which also drives the main bristle support 10. As FIGS. 2 and 3 show, provision is made on the bottom side of the auxiliary bristle support 13 for a drive coupling 21 which comprises a longitudinal clearance space 22 extending parallel to the pivot axis 19, in which the driver pin 50 is guided. For this purpose the drive shaft 15 has in the region of the passage hole a recess 53 such that the driver pin 50 lies free (cf. FIG. 4) and the passage hole, in which the driver pin 50 is received, is formed by two aligned passage hole sections. The longitudinal clearance space 22 is defined in the drawn embodiment by two post-shaped projections 23 and 24 between which the driver 50 is guided and which form a drive coupler for bristle support 10. The projections 23, 24 extend essentially parallel to the pivot axis 19 such that the clearance space or gap defined between the projections 23 and 24 extends likewise parallel to the pivot axis 19. Accordingly, only one component of the orbital drive motion of the driver 50 is transmitted, namely in the plane parallel to the longitudinal direction of the toothbrush and perpendicular to the pivot axis 19. The vertical component of the drive motion parallel to the plane of symmetry of the toothbrush is not transmitted because the driver 50 is free to move back and forth in this direction in the longitudinal clearance space 22 between the projections 23 and 24. In the longitudinal direction of the pin-shaped driver 50 the latter may also move freely back and forth between the projections 23 and 24 in order to permit the longitudinal motion of the driver 50 induced by the pickup 51. Finally the connection between the projections 23 and 24 and the driver 50 forms a flexible coupling which permits the driver 50 to pivot relative to the auxiliary bristle support 13 about an axis parallel to the pivot axis 19 in order to compensate the oscillating angle offset between the bristle support 13 and the driver 50. The inner sides of the projections 23 and 24 may be rounded for this purpose. The tubular brush head carrier 11 has underneath the auxiliary bristle support 13 a clearance hole through which the projections 23 and 24 of the auxiliary bristle support 13 extend.

FIGS. 5 to 12 show alternative bearing arrangements of the auxiliary bristle set 8 or the auxiliary bristle support 13. The toothbrush heads shown in these Figures are provided likewise for the toothbrush presented in FIG. 1, complying otherwise with the previously described toothbrush head, including the construction of the drive translator element 14 and its driver 50, hence to this extent reference is made to its description and the same reference numerals are used for corresponding components. In the Figures, only the pin-shaped driver 50 of the drive translator element is shown for the sake of simplicity.

Figure 5:
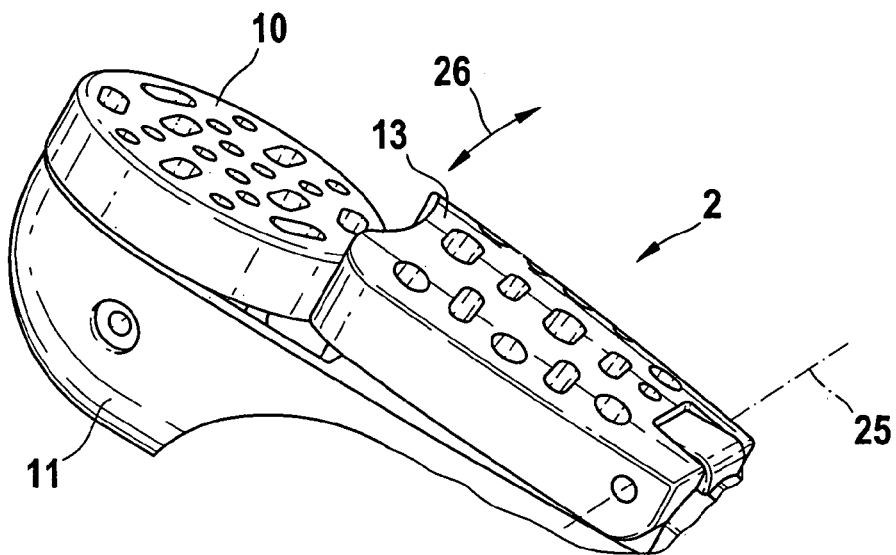
FIG. 5 is a fragmentary perspective view of a toothbrush head with two movably mounted bristle supports according to a further embodiment, in which the rear auxiliary bristle support is mounted and adapted to be driven for an up and down rocking motion about a transverse axis at its rear end section.

According to FIG. 5 the auxiliary bristle support 13 is mounted on the brush head carrier 11 for pivotal motion about a pivot axis 25 which extends essentially parallel to the plane defined by the auxiliary bristle support 13 and transverse to the longitudinal direction of the toothbrush. The auxiliary bristle support 13 has its rear end portion or edge, i.e., that close to the handpiece 1, pivotally mounted, with the result that it can perform an up and down rocking motion about the pivot axis 25. The portion of the auxiliary bristle support 13 close to the main bristle support 10 is able to rock up and down as per the arrow 26 with the result that the bristles of the auxiliary bristle set 8 perform a poking motion.

Figure 6:
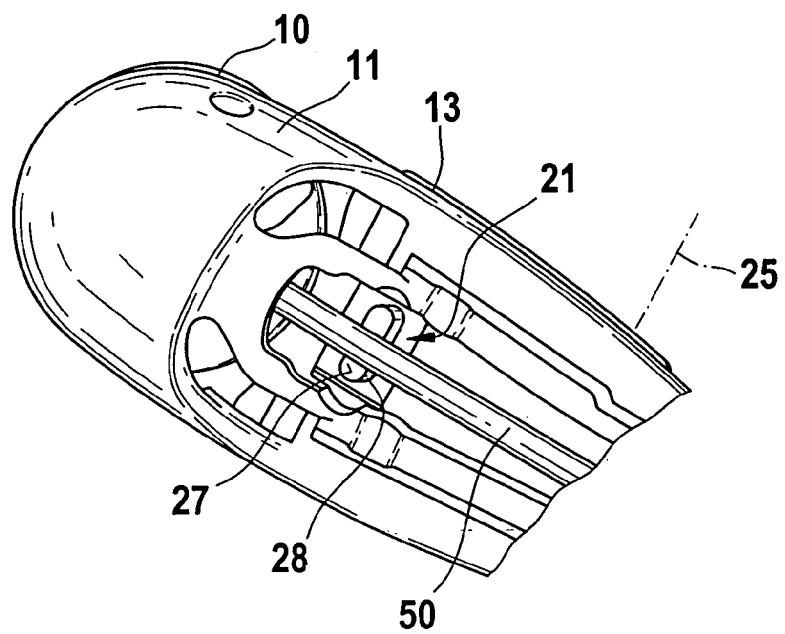
FIG. 6 is a fragmentary perspective view of the toothbrush head of FIG. 5 as seen looking in a different direction, showing the drive mechanism for the two bristle supports and in particular the coupling of the rear auxiliary bristle support to a driver.

To drive the auxiliary bristle support 13 about the pivot axis 25 in an oscillatory motion, provision is made on its bottom side for an engaging or sliding surface 27 as drive coupling, with which it sits on the driver 15 which also drives the main bristle support 10. As FIG. 6 shows, the engaging or sliding surface 27 is formed by the end of an elongated tappet or protuberance 28 which extends transverse to the longitudinal direction of the toothbrush and projects toward the driver 50. The surface of the tappet 28 may be of an essentially plane configuration. The driver 50 oscillating in an orbital path rides in transverse direction over the sliding surface 27, with the vertical component of the orbiting crank motion being transmitted to the tappet or protuberance 28, causing the auxiliary bristle support 13 to rock up and down, while the sliding surface 27 is held in engagement with the driver 50 by the reaction forces from cleaning the teeth, which forces act on the auxiliary bristle set. As the case may be, the auxiliary bristle support may be held biased by a spring, for example, which urges the auxiliary bristle support against the driver 50. Alternatively it would also be possible to provide instead of the sliding surface 27 a groove-shaped transverse recess in a corresponding section of the auxiliary bristle support 13 in which the driver 50 sits, with the result that the auxiliary bristle support would be urged upwards by the driver and actively drawn down. Such a transverse groove corresponds to the arrangement of two parallel sliding surfaces 27 between which the driver 50 is guided.

Figure 7:
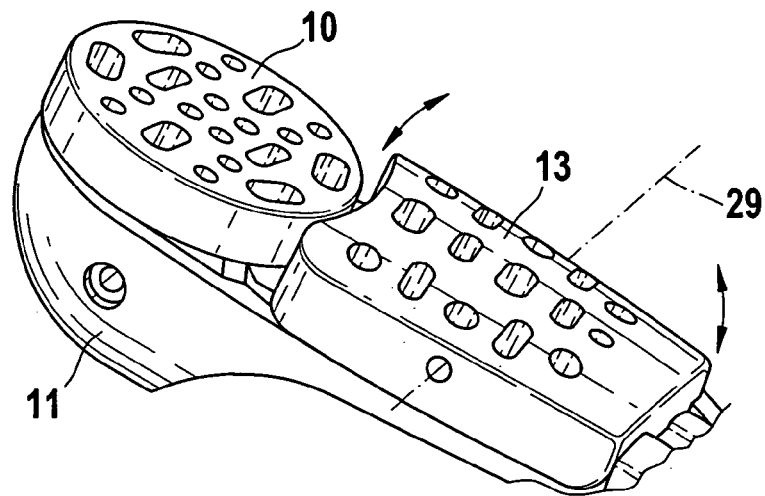
FIG. 7 is a fragmentary perspective view of a toothbrush head with two movably mounted bristle supports according to an alternative embodiment, in which the rear auxiliary bristle support is mounted approximately centrally for rocking motion about a transverse axis.
Figure 8:
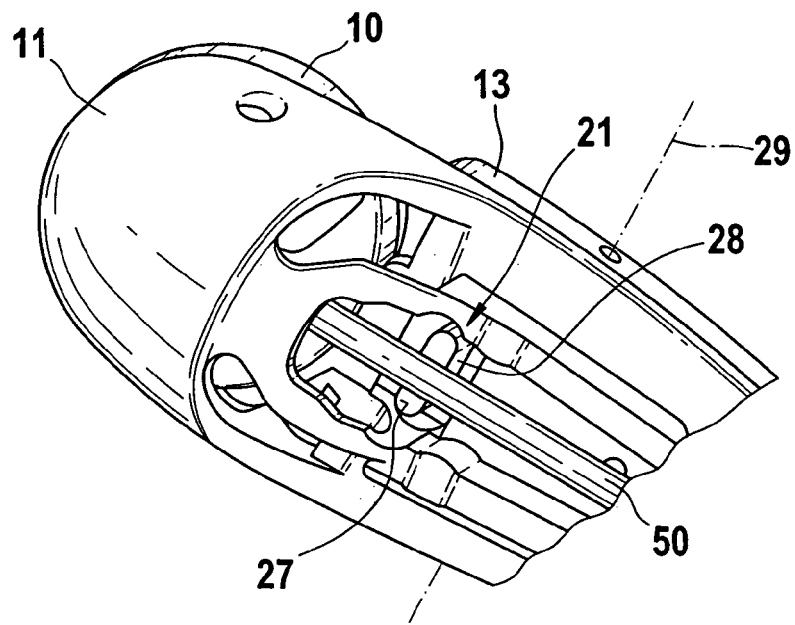
FIG. 8 is a fragmentary perspective view of the toothbrush head of FIG. 7 as seen looking in a different direction, showing the drive mechanism for the two bristle supports and in particular the coupling of the rear auxiliary bristle support to the drivers of the drive mechanism.

According to FIGS. 7 and 8 the auxiliary bristle support 13 may also be mounted approximately centrally about a transversely extending pivot axis 29 in the manner of a rocker. As in the embodiment previously described the pivot axis 29 extends transverse to the longitudinal direction of the toothbrush approximately in the plane defined by the auxiliary bristle support 13 or a plane parallel thereto, with the result that a portion of the auxiliary bristle support 13 close to the main bristle support 10 and an opposite portion of the auxiliary bristle support 13 close to the handpiece 1 perform up and down rocking movements in counter sequence. Like the previously described embodiment of FIGS. 5 and 6, the drive coupling of the auxiliary bristle support may be formed by a sliding surface 27 provided on a tappet 28, which slides on the driver 50. Considering that in this embodiment the reaction forces from cleaning the teeth act on either side of the pivot axis 29, the provision of a biasing device holding the auxiliary bristle support in engagement with the driver 50 may be useful. As the case may be, it is also possible to provide the previously described positive guidance by means of a transverse groove in which the driver sits.

Figure 9:
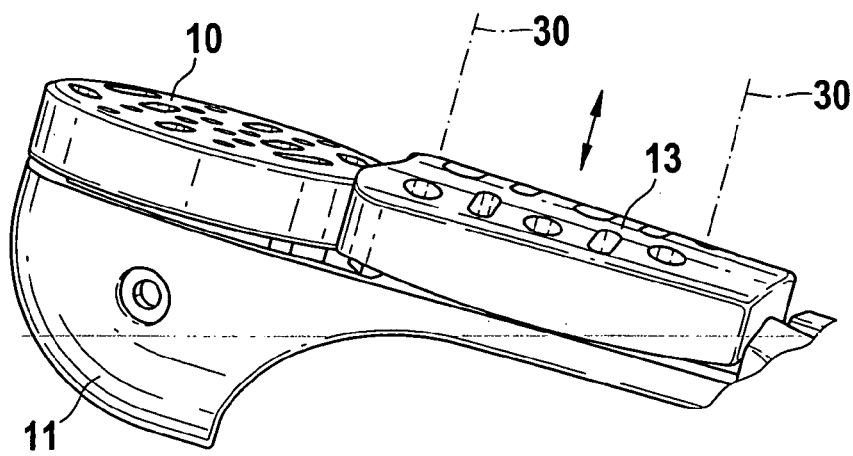
FIG. 9 is a fragmentary perspective view of a toothbrush head with two movably mounted bristle supports according to an alternative embodiment, in which the rear auxiliary bristle support is mounted for a raising and lowering motion about a translational motion axis essentially parallel to the main direction of the bristles.
Figure 10:
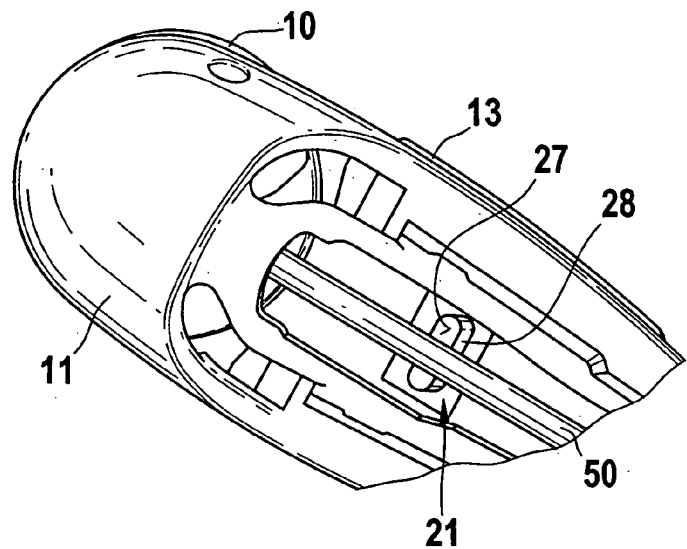
FIG. 10 is a fragmentary perspective view of the toothbrush head of FIG. 9 as seen looking in a different direction, showing the drive mechanism for the two bristle supports and in particular the coupling of the rear auxiliary bristle support to the drivers of the drive mechanism.

According to FIGS. 9 and 10 the auxiliary bristle support 13 may also be guided for translatory displacement on the brush head carrier 11. As FIG. 9 shows, the auxiliary bristle support 13 may be guided along two motion axes 30 which extend essentially perpendicular to the plane defined by the auxiliary bristle support. The sliding guide may be constructed, for example, as a cylindrical stud guide known in the art. The sliding guide axes 30 may be arranged on the longitudinal central plane of the toothbrush in a rear and front edge portion of the auxiliary bristle support 13, as is shown in FIG. 9. The auxiliary bristle support 13 may perform up and down stroke motions in accordance with its translational mobility, so that the auxiliary bristle set 8 on the auxiliary bristle support 13 makes poking movements.

The stroke motion of the auxiliary bristle support 13 is produced in this case too by coupling to the eccentric driver 50. As FIG. 10 shows, provision may be made on a bottom side of the auxiliary bristle support 13 for a sliding surface 27 which extends transverse to the longitudinal direction of the toothbrush and is formed by the surface of a tappet 28 projecting towards the driver 50. Conveniently, the tappet 28 is located approximately centrally underneath the auxiliary bristle set and centrally between the motion axes 30 such that a uniform distribution of force and skew-free motion can be obtained. The reaction forces from cleaning the teeth, which act on the auxiliary bristle set 8, hold the sliding surface 27 in engagement with the driver 50.

Figure 11:
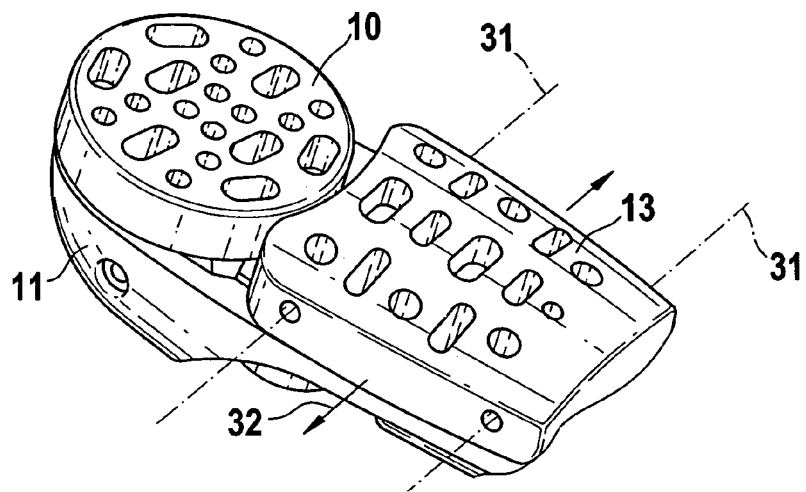
FIG. 11 a fragmentary perspective view of a toothbrush head with two movably mounted bristle supports according to a further embodiment, in which the rear auxiliary bristle support is mounted for a reciprocating motion about a translational motion axis transverse to the longitudinal direction of the toothbrush and transverse to the main direction of the bristles.
Figure 12:
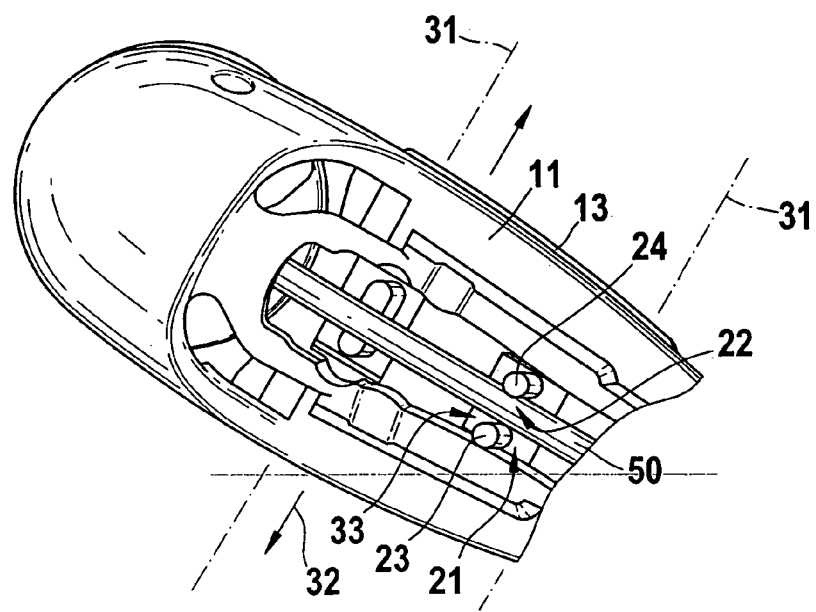
FIG. 12 is a fragmentary perspective view of the toothbrush head of FIG. 11, showing the drive mechanism for the two bristle supports and in particular the coupling of the rear auxiliary bristle support to the drivers.

FIGS. 11 and 12 show a further possible bearing arrangement of the auxiliary bristle support 13. In this case too the auxiliary bristle support 13 is mounted on the brush head carrier 11 for translatory displacement, which takes place along two parallel sliding guide axes 31 which extend in the plane defined by the auxiliary bristle support 13 transverse to the longitudinal direction of the toothbrush. As FIG. 11 shows, a rear end portion close to the handpiece 1 and an end portion of the auxiliary bristle support 13 close to the main bristle support 10 may be mounted by means of said sliding guide. In this case the auxiliary bristle support 13 is able to perform reciprocating movements laterally and transversely, as is indicated by the arrow 32.

The translationally oscillating drive motion of the auxiliary bristle support 13 is effected by the driver 50 in this case too. As FIG. 12 shows, the auxiliary bristle support 13 sits on the driver 15 by means of a transverse guide 33. Similar to the embodiment of FIGS. 2 and 3, the transverse guide 33 is defined by two parallel post-shaped projections 23 and 24 which define between themselves a gap or a longitudinal clearance space 22 extending essentially perpendicular to the plane of the auxiliary bristle support 13. The driver 50 is free to slide up and down between the two projections 23 and 24 in vertical direction, i.e., in the plane of longitudinal symmetry of the toothbrush. However, in a plane normal thereto, i.e., in a plane parallel to the two sliding guide axes 31, the drive motion of the driver 50 is transmitted such that the auxiliary bristle support 13 oscillates back and forth in the direction of the sliding guide axes 31.

Figure 13:
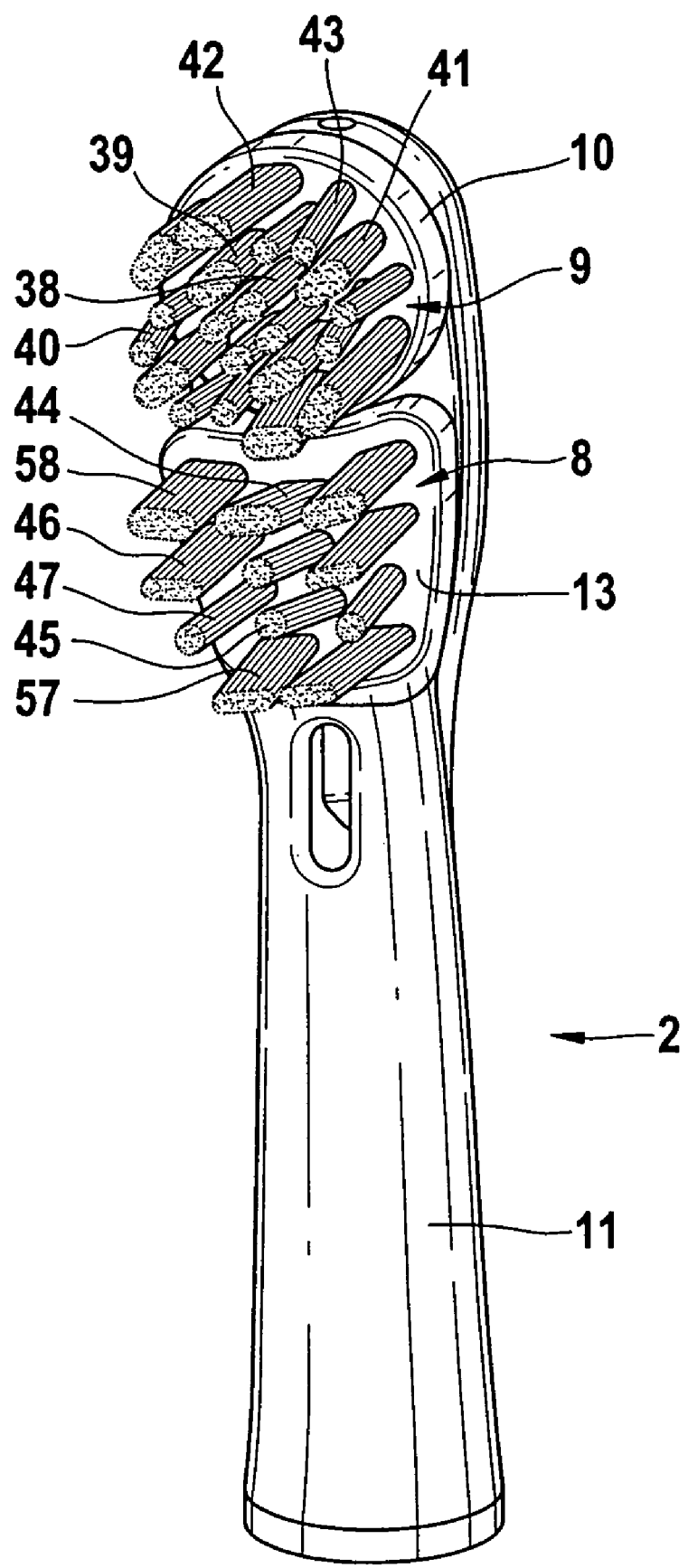
FIG. 13 is a perspective view of a toothbrush head of the toothbrush of FIG. 1, showing the arrangement of the bristle tufts on the two bristle supports.

One possible bristle array of the two bristle supports 10 and 13 is shown in FIG. 13. It will be understood that the bristle array of FIG. 13 may be provided on each of the previously described embodiments of the auxiliary bristle support or its bearing arrangement.

The main bristle set 9 drivable in an oscillatory rotational motion has an on the whole roughly circular cylindrical contour and is formed by a multiplicity of bristle tufts of various angles of tilt, various heights and various cross sections.

As FIG. 13 shows, central first bristle tufts 38 are arranged centrally around the axis of rotation of the main bristle support. They extend perpendicular to the plane defined by the bristle support 10 and have a roughly circular or slightly oval cross section. Four of these first bristle tufts 38 are provided. They lie centrally around the axis of rotation 19. Adjacent to the first bristle tufts 38 are second bristle tufts 39 which in the non-rotated position of the bristle support 10 lie on the longitudinal central axis of the toothbrush and in longitudinal direction in front of and respectively behind the first bristle tufts 38. As FIG. 13 shows, the second bristle tufts 39 have an oval cross section with a longitudinal axis extending transverse to the longitudinal axis of the toothbrush. The second bristle tufts 39 are arranged likewise perpendicular to the plane defined by the bristle support 10. Their distance from the axis of rotation 19 is larger than that of the first bristle tufts 38. The ratio of the contour length to the contour width is approximately two.

The other bristle tufts of the driven bristle set are tilted in varying orientations. The fourth bristle tufts 40, which are arranged radially outside the first bristle tufts 38, in a manner of speaking on a second bristle tuft ring, have a roughly circular cross section and are tilted radially outwardly, i.e., their free working ends are further removed from the axis of rotation of the bristle support than their fastening ends anchored in the bristle support 10. The angle of tilt is acute and amounts to less than 20°.

The third bristle tufts 41 are likewise tilted in a radially outward direction. However, they have an oval contour or an elongated cross section, the longitudinal axis of the cross section being radially oriented. The cross section of the third bristle tufts is about twice to three times longer than it is wide. The third bristle tufts 41 sit radially outside the first bristle tufts 38 and adjacent to them on a symmetry axis of the bristle set extending transverse to the longitudinal direction of the toothbrush.

The other bristle tufts of the bristle set 9 are likewise tilted but in circumferential direction around the axis of rotation 12. They form the outer edge or ring of the bristle set 9.

The fifth bristle tufts 42 have an oval contour or an elongated cross section which is oriented roughly tangentially to the edge of the bristle support 10. In cross section the bristle tufts 42 are about twice to three times longer than they are wide. As FIG. 1 shows, the fifth bristle tufts 42 are arranged in pairs in the region of the longitudinal axis of the toothbrush when the bristle set 9 is in non-rotated position. They are tilted in pairs towards each other such that their free working ends are closer together than their fastening ends anchored in the bristle support 10.

Finally, provision is made for sixth bristle tufts 43 which lie likewise on the outer edge of the bristle set and are tilted in circumferential direction around the axis of rotation 12. However, they have a roughly circular cross section and are arranged in pairs on either side of the third bristle tufts 41 and tilted towards them likewise in opposite directions. The angles of tilt of the outer lying bristle tufts 43 and 42, which are inclined in circumferential direction, are likewise acute and may amount to less than 20° relative to the perpendicular through the plane defined by the bristle support 10.

As FIGS. 2 and 13 show, the bristle tufts arranged on the movable bristle support 10 have two lengths. The outer positioned fifth bristle tufts 42 lying at the very front and rear in longitudinal direction, whose free ends all lie in one plane, are longer than the remaining bristle tufts. The free ends of the fifth bristle tufts 42 define a plane. The difference in height between the bristle tufts lies in the region from 0.5 mm to 2.5 mm, preferably around 1.0 mm to 1.5 mm.

The bristle tufts of the auxiliary bristle set 8 are likewise of varying cross sections in terms of contour and surface area and are arranged in addition likewise at varying angles of tilt. Also, provision is made for bristle tufts of varying lengths, as will be described in the following.

As FIG. 1 shows, provision is made in the auxiliary bristle set 8 roughly speaking for three rows of bristle tufts, all of which extend approximately in the longitudinal direction of the toothbrush. The middle row lies on the longitudinal central axis of the auxiliary bristle support 13 while the two outer rows are spaced therefrom in transverse direction.

In the middle bristle row all the bristle tufts are tilted toward the main bristle set. The bristle tufts have various cross-sectional areas. A first bristle tuft 44 of the fixed bristle set 8 has an oval cross section, whose longitudinal axis is approximately twice as long as its transverse axis, and sits in the middle row closer to the main bristle set 9 than bristle tufts 45 hereinafter referred to as fourth bristle tufts, which are likewise tilted rearwardly towards the handpiece. The fourth bristle tufts 45 have a round or, as the case may be, slightly oval cross section, but are constructed to be far slimmer and have a smaller cross-sectional area than the first bristle tufts 44.

The two outer rows of bristle tufts of the fixed bristle set 8, which converge slightly towards the handpiece, as is shown in FIG. 1, are comprised of second, third, fifth and sixth bristle tufts. Second bristle tufts 46 have an oval cross section with a relatively slim contour. The longitudinal axis of the longitudinal cross-sectional contour amounts roughly to three times the width of the cross-sectional contour. The third bristle tufts 47 have a roughly circular cross section, with the diameter of the cross section amounting roughly to half the longitudinal axis of the cross section of the second bristle tufts 46. The third bristle tufts are outwardly tilted away from the longitudinal central plane. Fifth bristle tufts 57 are arranged nearest to the handpiece and have a cross section roughly the same as the second bristle tufts 46 but they are inwardly tilted towards the longitudinal central plane (cf. FIG. 1). By contrast, the other bristle tufts of the outer rows are not tilted. The sixth bristle tufts 58 are the thickest bristle tufts and arranged in the outer rows nearest to the main bristle set 9. They have an elongated cross section with a longitudinal axis that is transverse to slightly oblique in relation to the longitudinal central plane.

As FIG. 1 shows, the bristle tufts of the outer two rows are arranged at varying distances to the longitudinal central axis of the brush head 2. The distance to the longitudinal central axis decreases towards the handpiece 1. However, the bristle tufts 47 are arranged in a row one behind the other such that their contour lies at least partly roughly behind the contour of the next bristle tufts respectively in the row.

The bristle tufts of the auxiliary bristle set 8 define two working planes, as FIG. 2 shows. The circular third bristle tufts 47 and the oval, thick sixth bristle tufts 58 in the outer rows as well as the thicker first bristle tufts 44 and the round bristle tufts 45 in the middle row are shorter, defining with their free working ends a lower plane that coincides with the plane defined by the first, second, third and fourth as well as sixth bristle tufts of the main bristle set 9. A higher, second plane is defined by contrast by the longer slim oval bristle tufts 46 and 57 in the two outer rows. This higher plane coincides with the plane that is defined by the longer fifth bristle tufts of the main bristle set 9. Hence in the auxiliary bristle set 8 the slimmer oval bristle tufts are of greater length than the thicker bristle tufts.

Unlike the main bristle set 9 the auxiliary bristle set 8 has no circular contour but an on the whole elongated contour which at its end close to the rotary bristle set 9 embraces the latter. A number of embodiments have been described. Nevertheless, it will be understood that various modifications may be made without departing from the spirit and scope of this disclosure.

The invention claimed is:

1. A toothbrush head for an electric toothbrush, the toothbrush head comprising a brush head carrier that is releasably connectable to a hand piece of an electric toothbrush, the brush head carrier comprising:
   a brush head carrier housing having a free end configured to be releasably connected to an electric toothbrush hand piece;
   a translator element rotatable about a longitudinal rotation axis within the brush head carrier housing;
   a plurality of bristle supports that each carry a respective bristle set and are movably mounted on the brush head carrier housing; and
   a plurality of drive couplers, each drive coupler being coupled to a respective bristle support and eccentrically coupled to the translator element by an eccentric driver, such that each of the bristle supports is oscillated in response to rotation of the translator element, at least one of the bristle supports coupled so as to rotate in oscillation about an axis of rotation extending transverse to the longitudinal rotation axis of the translator element;
   wherein the plurality of bristle supports includes
      a main bristle support rotatable about an axis of rotation essentially perpendicular to the longitudinal rotation axis of the translator element; and
      an auxiliary bristle support pivoted about a pivot axis essentially perpendicular to the longitudinal rotation axis of the translator element and disposed near an edge of the auxiliary bristle support nearest the main bristle support, such that an end of the auxiliary bristle support remote from the main bristle support oscillates laterally as the auxiliary bristle support pivots about the pivot axis; and
   wherein the pivot axis is arranged approximately parallel to a main bristle direction of bristles of the auxiliary bristle support.

2. The toothbrush head of claim 1 wherein the eccentric driver comprises a driver pin.

3. The toothbrush head of claim 2 wherein the driver pin moves in an orbit that includes at least a partial cylinder segment relative to the rotation axis of the translator element.

4. The toothbrush head of claim 2 wherein the driver pin is coupled to at least one of the drive couplers at a coupling that allows for relative pivoting of the coupled driver coupler with respect to the driver pin, to compensate for angulation between the eccentric driver and a corresponding bristle support.

5. The toothbrush head of claim 1 wherein the brush head carrier is non-rotatably coupled to the hand-piece.

6. The toothbrush head of claim 1 wherein each of the bristle supports has its own axis of motion transverse to the longitudinal axis.

7. The toothbrush head of claim 1 wherein the main bristle support is disposed at a distal end of the brush head carrier.

8. The toothbrush head of claim 1 wherein at least one of the drive couplers is coupled to the eccentric driver with a translational degree of freedom, allowing translational motion in a direction transverse to the longitudinal rotation axis of the translator element.

9. The toothbrush head of claim 8 wherein the eccentric driver is guided within a longitudinally slotted clearance space defined within said at least one of the drive couplers.

10. The toothbrush head of claim 8 wherein one of the bristle supports defines a sliding surface that extends transverse to a longitudinal axis of the toothbrush head and on which the eccentric driver is adapted to slide.

11. The toothbrush head of claim 10 further including a biasing device biasing the sliding surface against the eccentric driver.

12. The toothbrush head of claim 1 wherein at least one of the drive couplers is constructed such that forces and movements are transmitted exclusively in a direction transverse to a longitudinal direction of the toothbrush head.

13. The toothbrush head of claim 12 wherein the drive couplers are free to move in a plane containing a longitudinal direction of the toothbrush head and being force-transmitting in a plane perpendicular thereto.

14. The toothbrush head of claim 1 wherein at least one of the drive couplers is constructed such that forces and movements are transmitted in a direction transverse to a longitudinal direction of the toothbrush head and forces are transmitted in the longitudinal direction of the toothbrush head, and wherein the driver is mounted on the translator element for displacement in the longitudinal direction.

15. The toothbrush head of claim 1 wherein at least one of the drive couplers is integral with its respective bristle support and in positive engagement with the driver.

16. The toothbrush head of claim 1 further comprising a spring biasing the eccentric driver against at least one of the bristle supports.

17. The toothbrush head of claim 1 wherein the translator element comprises a disengageable rotary coupling adapted to engage a drive element of a toothbrush hand piece.

18. The toothbrush head of claim 1 wherein at least one of the bristle supports carries bristle tufts tilted in varying orientations, of varying cross sections, of varying lengths, or tilted at varying angles.

19. An electric toothbrush comprising:
   a hand piece equipped with an electric drive; and
   the toothbrush head of claim 1 releasably secured to the hand piece.

20. A toothbrush head for an electric toothbrush, the toothbrush head comprising a brush head carrier that is releasably connectable to a hand piece of an electric toothbrush, the brush head carrier comprising:
   a brush head carrier housing having a free end configured to be releasably connected to an electric toothbrush hand piece;
   a translator element rotatable about a longitudinal rotation axis within the brush head carrier housing;
   a plurality of bristle supports that each carry a respective bristle set and are movably mounted on the brush head carrier housing; and
   a plurality of drive couplers, each drive coupler being coupled to a respective bristle support and eccentrically coupled to the translator element by an eccentric driver, such that each of the bristle supports is oscillated in response to rotation of the translator element, at least one of the bristle supports coupled so as to rotate in oscillation about an axis of rotation extending transverse to the longitudinal rotation axis of the translator element;

wherein the plurality of bristle supports includes
a main bristle support rotatable about an axis of rotation essentially perpendicular to the longitudinal rotation axis of the translator element; and
an auxiliary bristle support pivoted about a pivot axis essentially perpendicular to the longitudinal rotation axis of the translator element and disposed near an edge of the auxiliary bristle support nearest the main bristle support, such that an end of the auxiliary bristle support remote from the main bristle support oscillates laterally as the auxiliary bristle support pivots about the pivot axis;

wherein at least one of the drive couplers is coupled to the eccentric driver with a translational degree of freedom, allowing translational motion in a direction transverse to the longitudinal rotation axis of the translator element; and wherein one of the bristle supports defines a sliding surface that extends transverse to a longitudinal axis of the toothbrush head and on which the eccentric driver is adapted to slide, the toothbrush head further including a biasing device biasing the sliding surface against the eccentric driver.

21. A toothbrush head for an electric toothbrush, the toothbrush head comprising a brush head carrier that is releasably connectable to a hand piece of an electric toothbrush, the brush head carrier comprising:
a translator element rotatable about a longitudinal rotation axis within the brush head carrier and carrying a driver eccentrically disposed with respect to a rotational axis of the translator element;
a plurality of bristle supports that carry a respective bristle set and are movably mounted on the brush head carrier; and
a plurality of drive couplers, each drive coupler being coupled to a respective bristle support and eccentrically coupled to the translator element by the driver, such that each of the bristle supports is oscillated in response to rotation of the translator element;
wherein at least one of the drive couplers is constructed such that forces and movements are transmitted in a direction transverse to a longitudinal direction of the toothbrush head and forces are transmitted in the longitudinal direction of the toothbrush head, and wherein the driver is mounted on the translator element for displacement in the longitudinal direction.

22. A toothbrush head for an electric toothbrush, the toothbrush head comprising a brush head carrier that is releasably connectable to a hand piece of an electric toothbrush, the brush head carrier comprising:
a translator element rotatable about a longitudinal rotation axis within the brush head carrier and carrying an eccentric driver;
a plurality of bristle supports that carry a respective bristle set and are movably mounted on the brush head carrier;
a plurality of drive couplers, each drive coupler being coupled to a respective bristle support and eccentrically coupled to the translator element by the eccentric driver, such that each of the bristle supports is oscillated in response to rotation of the translator element; and
a spring disposed between the translator element and the eccentric driver and biasing the eccentric driver against at least one of the bristle supports.

* * * * *